US009366551B2

(12) United States Patent
Fujita et al.

(10) Patent No.: US 9,366,551 B2
(45) Date of Patent: Jun. 14, 2016

(54) OPTICAL SENSOR HAVING A CHARACTERISTIC CHANGING PART IN A CHARACTERISTIC LIGHT GUIDING MEMBER

(71) Applicant: OLYMPUS CORPORATION, Tokyo (JP)

(72) Inventors: Hiromasa Fujita, Hachioji (JP); Eiji Yamamoto, Musashimurayama (JP)

(73) Assignee: OLYMPUS CORPORATION

( * ) Notice: Subject to any disclaimer, the term of this patent is extended or adjusted under 35 U.S.C. 154(b) by 139 days.

(21) Appl. No.: 14/445,483

(22) Filed: Jul. 29, 2014

(65) Prior Publication Data

US 2014/0332675 A1    Nov. 13, 2014

Related U.S. Application Data

(63) Continuation of application No. PCT/JP2013/050832, filed on Jan. 17, 2013.

(30) Foreign Application Priority Data

Jan. 30, 2012    (JP) .................................. 2012-017178

(51) Int. Cl.
*G01D 5/353*    (2006.01)
*G01B 11/16*    (2006.01)
*G01D 5/26*    (2006.01)

(52) U.S. Cl.
CPC ................ *G01D 5/353* (2013.01); *G01B 11/16* (2013.01); *G01D 5/268* (2013.01); *G01D 5/35306* (2013.01); *G01D 5/35367* (2013.01)

(58) Field of Classification Search
CPC . G01D 5/268; G01D 5/353316; G01D 5/353; G01B 11/16; G01B 11/18; G01B 11/24
USPC ....................... 250/227.14–227.19; 385/8–13
See application file for complete search history.

(56) References Cited

U.S. PATENT DOCUMENTS

| | | | |
|---|---|---|---|
| 5,216,240 A | * | 6/1993 | Clift ................... G01D 5/35383 250/227.16 |
| 5,513,913 A | | 5/1996 | Ball et al. |
| 5,724,462 A | | 3/1998 | Ido et al. |

FOREIGN PATENT DOCUMENTS

| JP | 57-141604 A | 9/1982 |
|---|---|---|
| JP | H01-273010 A | 10/1989 |

(Continued)

OTHER PUBLICATIONS

English translation of International Preliminary Report on Patentability together with the Written Opinion dated Aug. 14, 2014 received in related International Application No. PCT/JP2013/050832.

(Continued)

*Primary Examiner* — Que T Le
(74) *Attorney, Agent, or Firm* — Scully, Scott, Murphy & Presser, PC

(57) ABSTRACT

An optical sensor has a light source, a characteristic light-guiding member, a characteristic changing part, a detecting unit, and an optical connecting unit. The optical connecting unit has a light branching unit configured to branch the light emitted from the light source to the characteristic light-guiding member, and branches the light guided by the characteristic light-guiding member to the detecting unit.

8 Claims, 11 Drawing Sheets

(56) References Cited

FOREIGN PATENT DOCUMENTS

| | | |
|---|---|---|
| JP | H02-050106 A | 2/1990 |
| JP | H02-089331 A | 3/1990 |
| JP | 06-109935 A | 4/1994 |
| JP | 8-506185 A | 7/1996 |
| JP | 08-288541 A | 11/1996 |
| JP | 09-096746 A | 4/1997 |
| JP | 2003-075133 A | 3/2003 |
| JP | 2005-084347 A | 3/2005 |
| JP | 2007-143600 A | 6/2007 |
| JP | 2008-190910 A | 8/2008 |
| WO | 94/17366 A1 | 8/1994 |

OTHER PUBLICATIONS

International Search Report dated Feb. 26, 2013 issued in PCT/JP2013/050832.
Chinese Office Action dated Sep. 1, 2015 issued in CN 201380006915.7.
Japanese Office Action dated Jan. 5, 2016 from related Japanese Patent Application No. 2012-017178, together with an English language translation.
Chinese Office Action dated Jan. 25, 2016 from related Chinese Patent Application No. 201380006915.7, together with an English language translation.

* cited by examiner

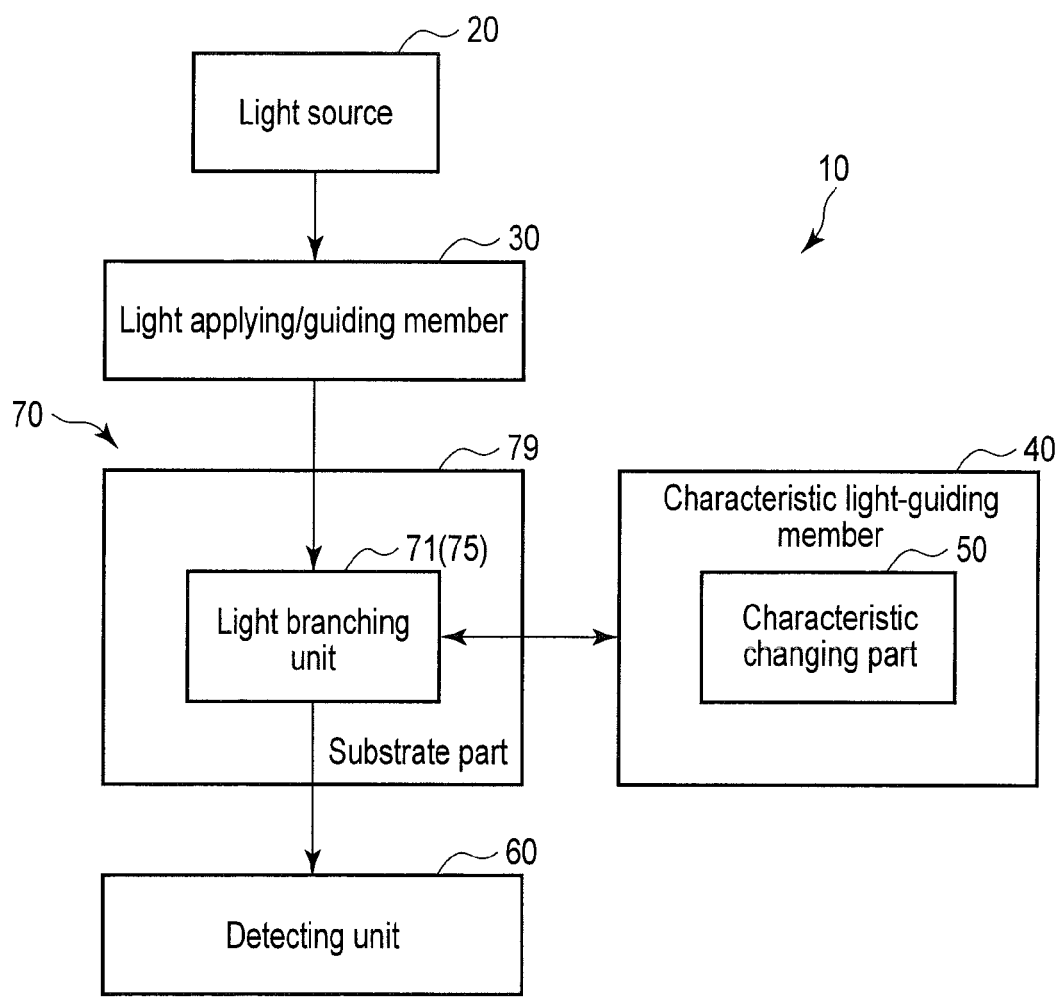
F I G. 1A

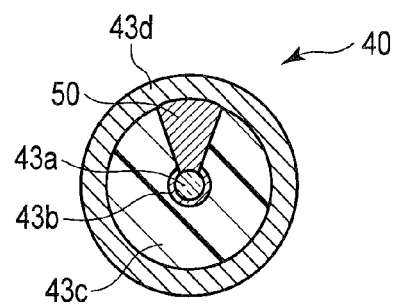
F I G. 1C
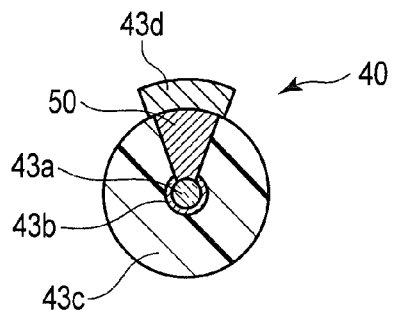
F I G. 1D
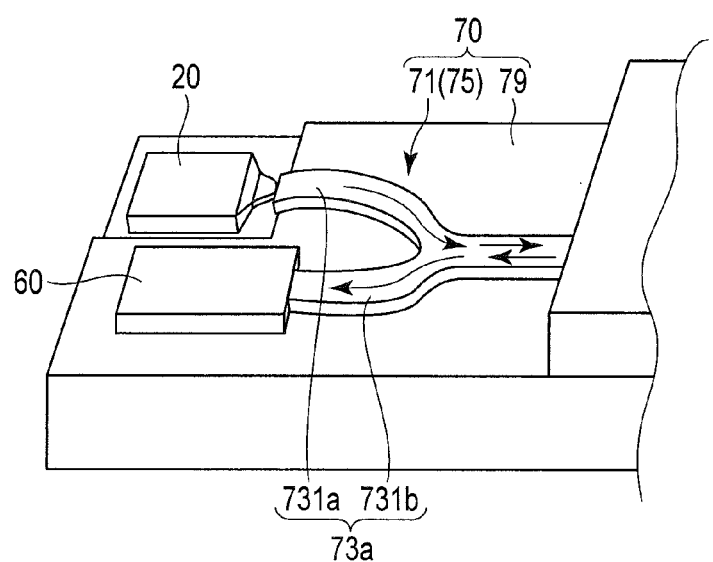
F I G. 1E

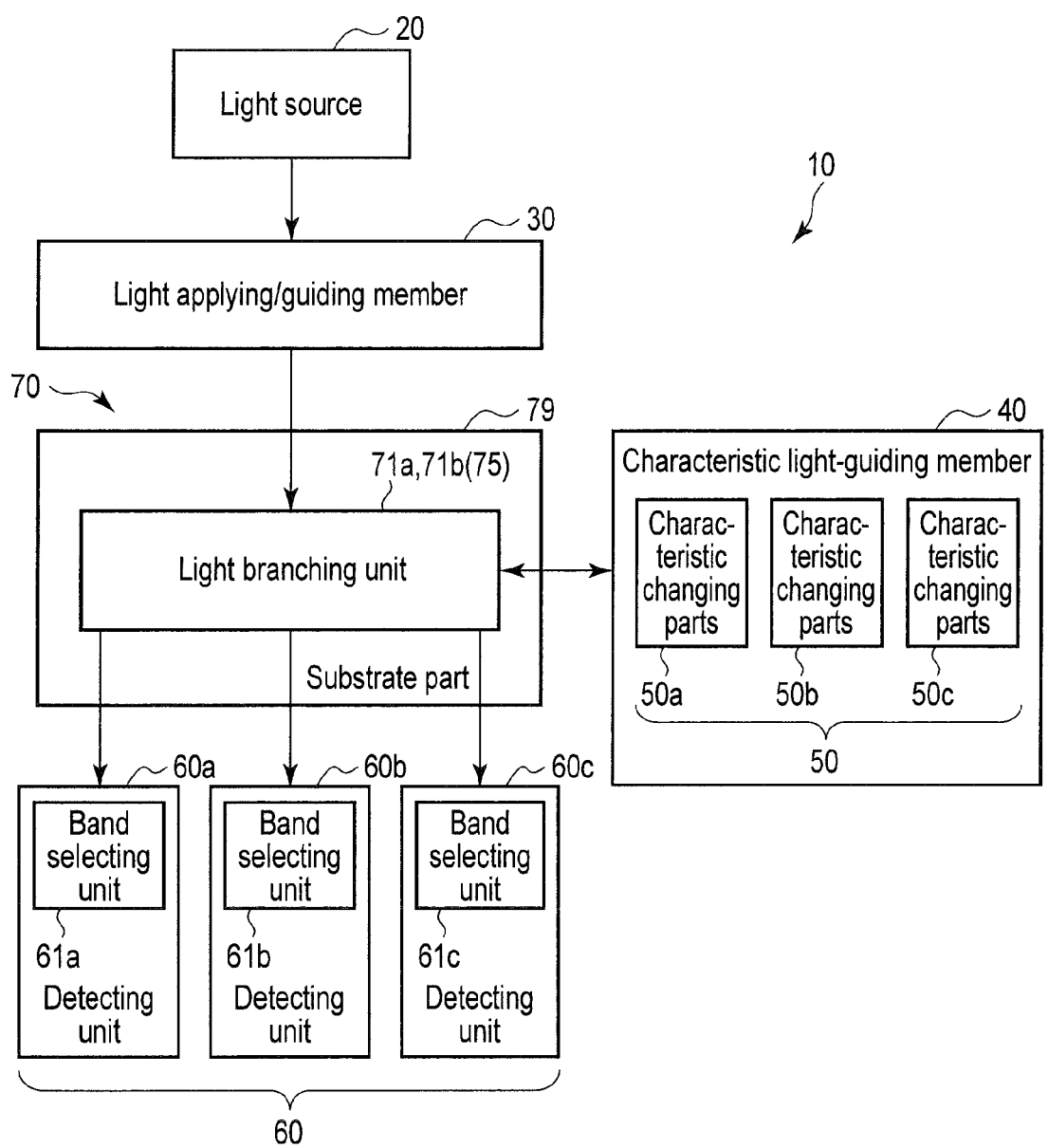
F I G. 2A

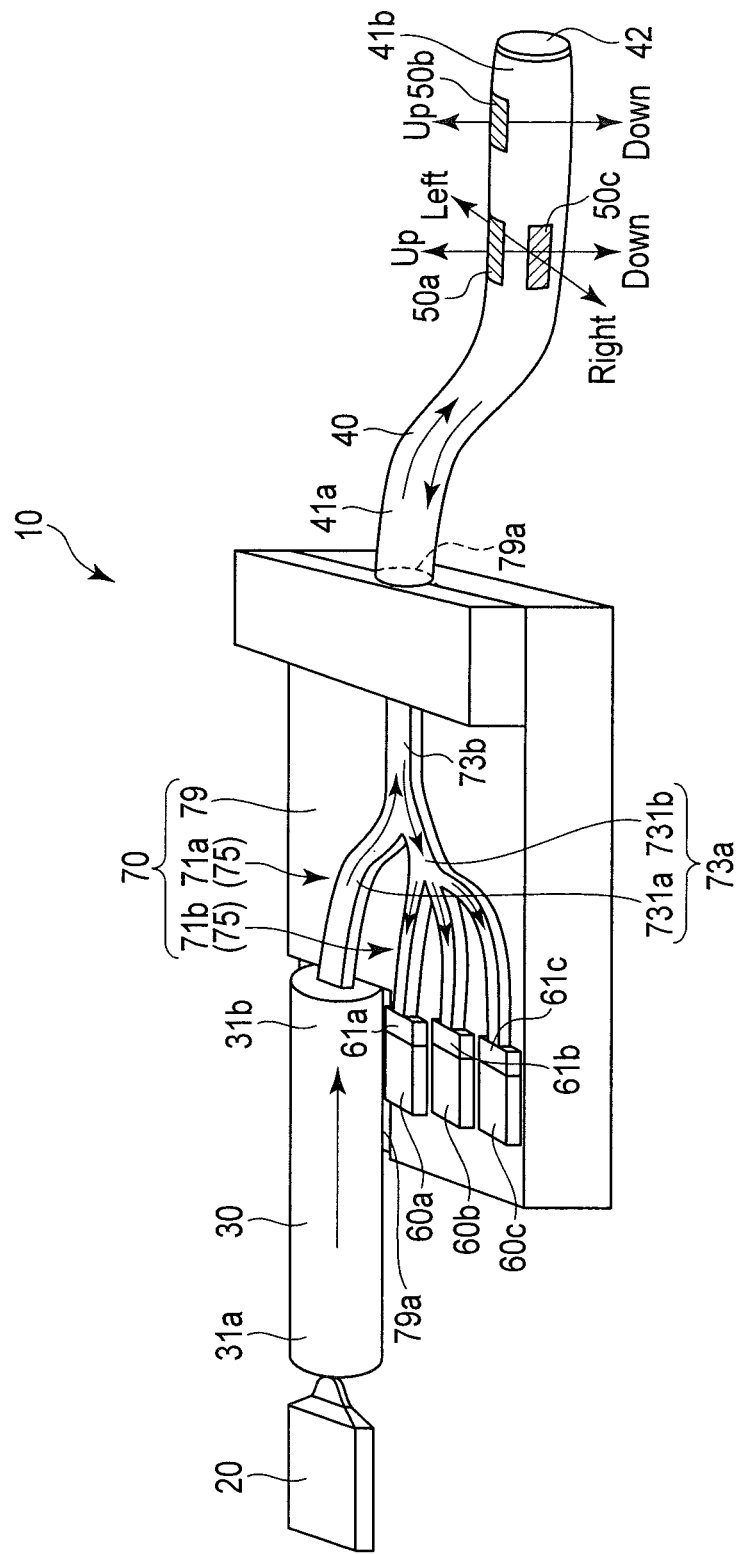
F I G. 2B

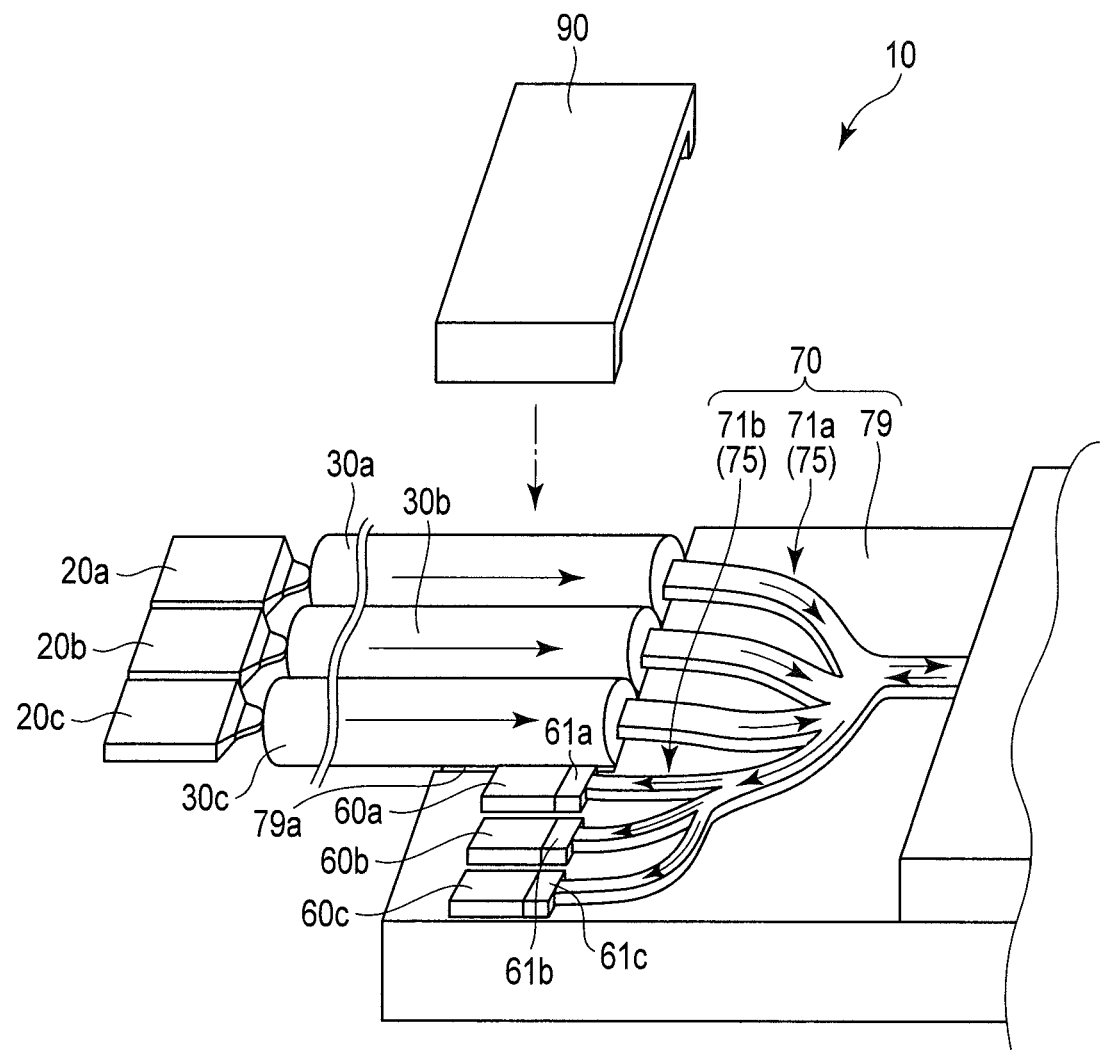
F I G. 2C

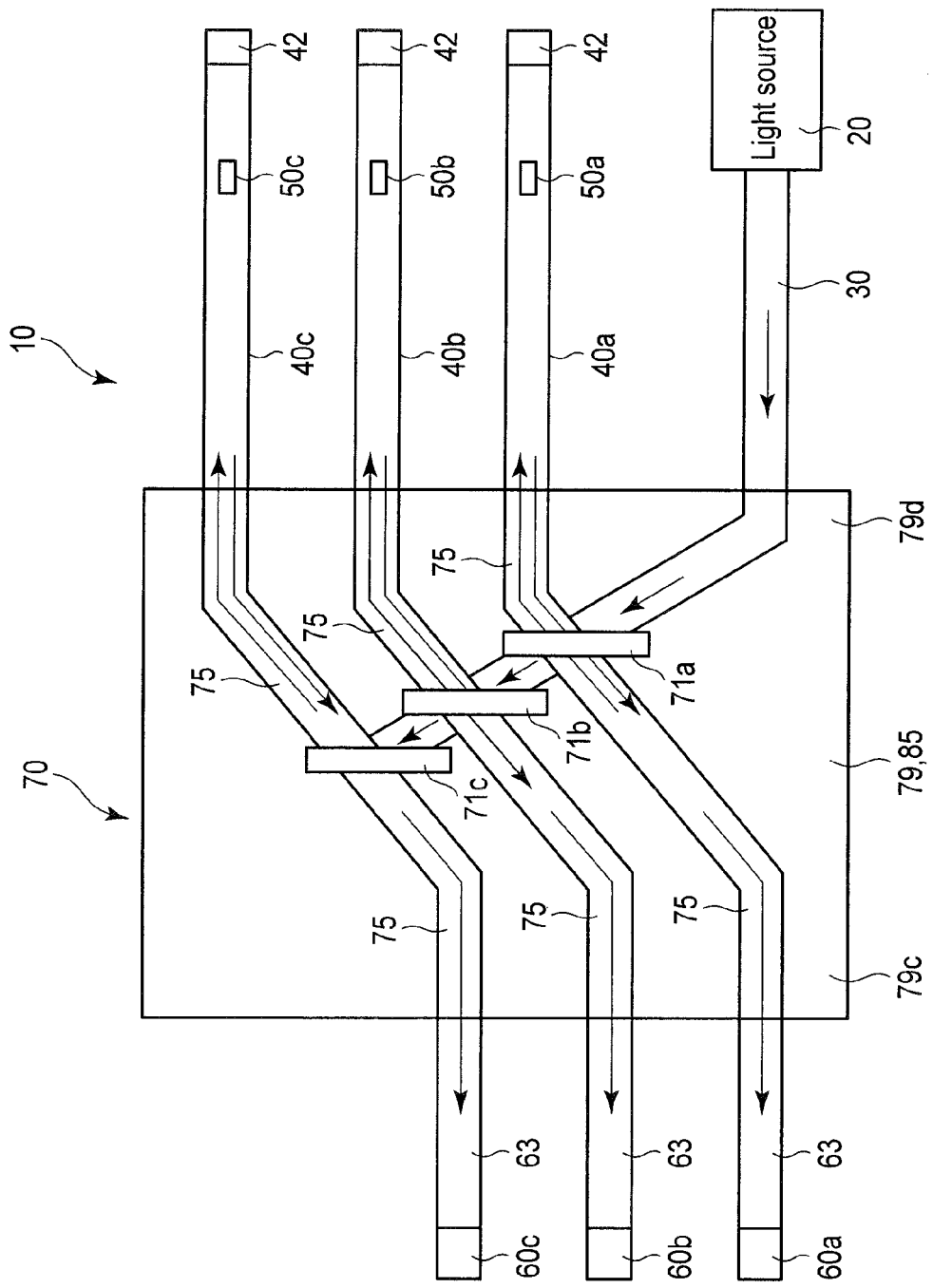
F I G. 4A

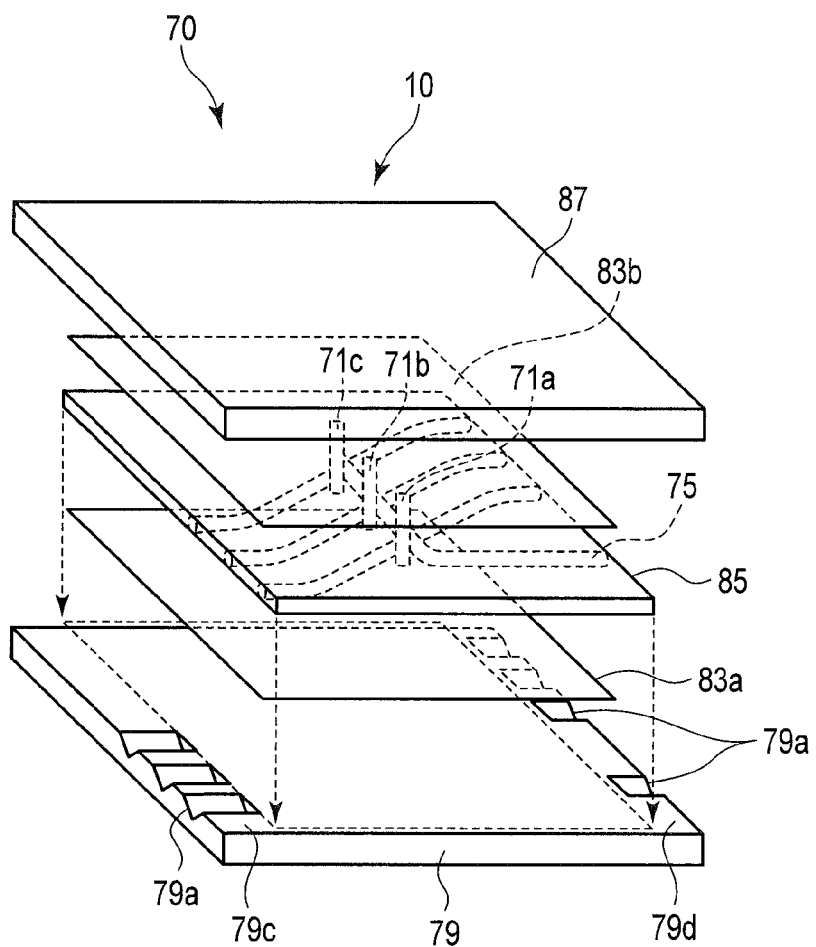
F I G. 4C

OPTICAL SENSOR HAVING A CHARACTERISTIC CHANGING PART IN A CHARACTERISTIC LIGHT GUIDING MEMBER

CROSS-REFERENCE TO RELATED APPLICATIONS

This application is a Continuation application of PCT Application No. PCT/JP2013/050832, filed Jan. 17, 2013 and based upon and claiming the benefit of priority from prior Japanese Patent Application No. 2012-017178, filed Jan. 30, 2012, the entire contents of all of which are incorporated herein by reference.

BACKGROUND OF THE INVENTION

1. Field of the Invention

This invention relates to an optical sensor.

2. Description of the Related Art

For example, Jpn. Pat. Apply. KOKAI Publication 57-141604 discloses an optical fiber. As shown in FIG. 5A, the optical fiber 101 has a core 101a, a cladding 101b covering the core 101a, and a light absorbing part 101c which is provided in the cladding 101b.

How light propagates in the optical fiber 101 will be explained.

As shown in FIG. 5A, in the case, the optical fiber 101 extends straight, light 103a propagating in the axial direction of the optical fiber 101 is guided at all. Light 103b propagating at a first angle to the axial direction is absorbed by the light absorbing part 101c. Light 103c propagating at a second angle to the axial direction is not absorbed by the light absorbing part 101c, is totally reflected by the cladding 101b and is guided forwards.

As shown in FIG. 5B, the optical fiber 101 may be bent at the light absorbing part 101c. In this case, lights 103, 103b and 103c propagate toward the light absorbing part 101c. As a result, the lights 103, 103b and 103c are absorbed by the light absorbing part 101c, and will no longer propagate.

The amount of light guided is thus controlled.

The optical fiber 101 so configured may be used in such a curvature measuring device 110 as shown in FIG. 5C. The device is a representative optical sensor which measures amount of displacement of the optical fiber 101. The curvature measuring device 110 shown in FIG. 5C has an optical fiber 101 shown in FIG. 5A and laid along a rail 111, a laser light source 113 connected to one end part of the optical fiber 101, and a photoelectric transducer device 115 connected to the other end part of the optical fiber 101. The optical fiber 101 is bent in compliance with the curvature of the rail 111. In proportion to the curvature of the rail 111, the light decreases in amount as it propagates in the optical fiber 101 from the laser light source 113 to the photoelectric transducer device 115. The photoelectric transducer device 115 measures the decrease in the amount of light. From the decrease in the amount of light, the curvature of the rail 111 and the downward flexure of the rail 111 will be determined when a train passes through.

As shown in FIG. 5C, for the optical sensor is arranged in the outdoor, the optical sensor cannot easily be incorporated in small high-precision devices in view of the arrangement of the optical fiber 101. In the optical sensor shown in FIG. 5C, the laser light source 113 is arranged at one end part of the optical fiber 101, and the photoelectric transducer device 115 is arranged at the other end part of the optical fiber 101. The optical sensor shown in FIG. 5C is inevitably large.

In view of the above, this invention has been made to provide a small optical sensor that can be incorporated in small high-precision devices.

BRIEF SUMMARY OF THE INVENTION

An aspect of an optical sensor of the present invention includes a light source configured to emit light; a characteristic light-guiding member configured to guide the light emitted from the light source; a characteristic changing part arranged in the characteristic light-guiding member and configured to change an optical characteristic of the light in accordance with how much the characteristic light-guiding member is bent; a detecting unit configured to detect the light changed in optical characteristic by the characteristic changing part and guided by the characteristic light-guiding member; and an optical connecting unit configured to connect optically the light source, the characteristic light-guiding member and the detecting unit, wherein the optical connecting unit has a light branching unit configured to branch the light emitted from the light source to the characteristic light-guiding member, and to branch the light guided by the characteristic light-guiding member to the detecting unit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic diagram showing an optical sensor according to a first embodiment of this invention;

FIG. 1C is a sectional view of a characteristic light-guiding member including a characteristic changing part;

FIG. 1D is a sectional view of the characteristic light-guiding member including a characteristic changing part;

FIG. 1E is a schematic perspective view of the optical sensor, showing that the light source shown in FIG. 1B is directly and optically connected to the optical connecting part;

FIG. 2A is a schematic diagram showing an optical sensor according to a second embodiment of this invention;

FIG. 2B is a schematic perspective view of the optical sensor according to the second embodiment;

FIG. 2C is a schematic perspective view of an optical sensor in which a plurality of light sources and a plurality of light-guiding members are arranged;

FIG. 4A is a schematic diagram showing an optical sensor according to a fourth embodiment of this invention;

FIG. 4C is an exploded perspective view of the optical sensor shown in FIG. 4B;

DETAILED DESCRIPTION OF THE INVENTION

Embodiments of this invention will be described in detail, with reference to the accompanying drawings.

First Embodiment

[Configuration]

The first embodiment of this invention will be described, with reference to FIG. 1A, FIG. 1B, FIG. 1C and FIG. 1D.

Figure 1B:
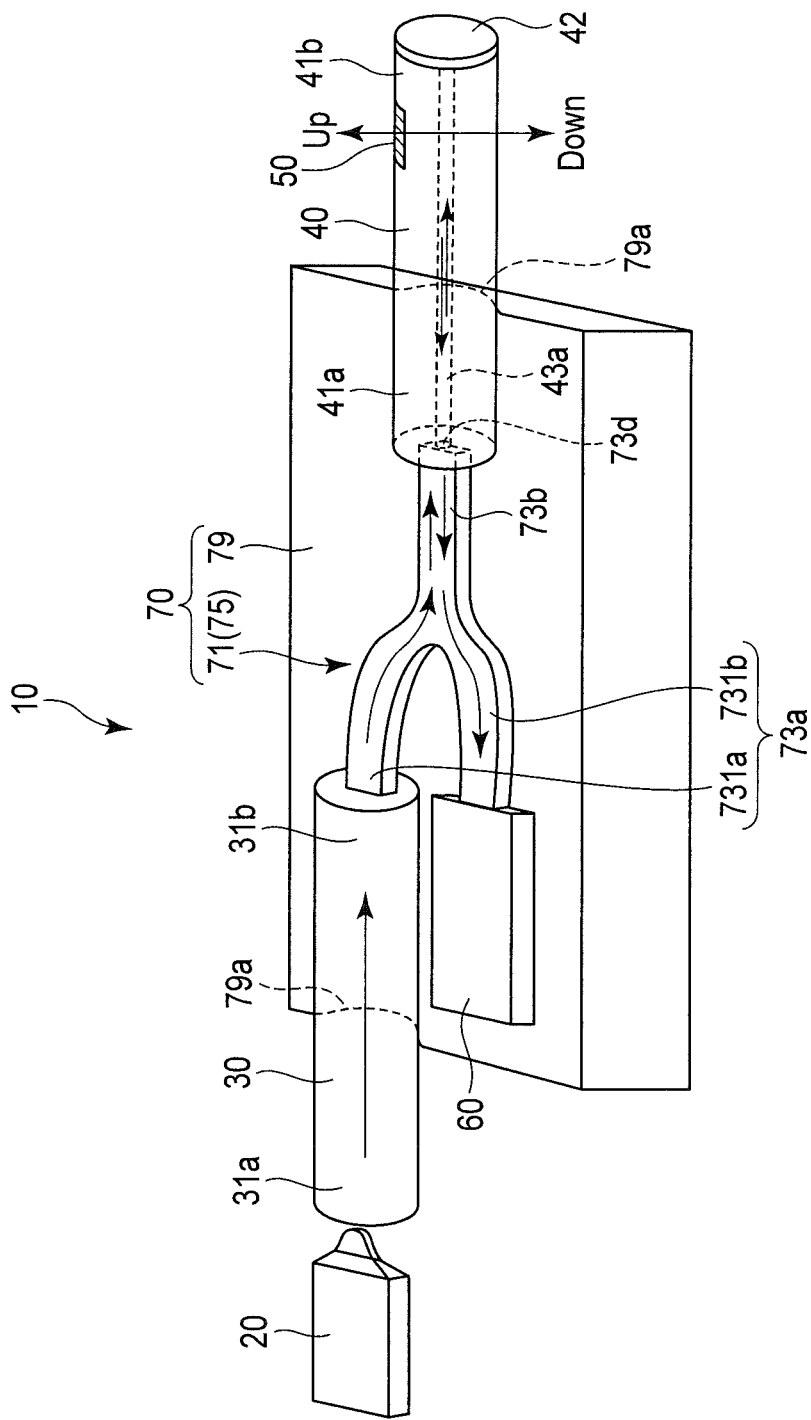
FIG. 1B is a schematic perspective view of the optical sensor shown in FIG. 1A.

As FIG. 1A and FIG. 1B show, the optical sensor 10 has a light source 20 for emitting light, a light supplying/guiding member 30 for guiding the light emitted from the light source 20 to supply the light, and a characteristic light-guiding member 40 for further guiding the light guided by the light supplying/guiding member 30. The optical sensor 10 further has a characteristic changing part 50, a detecting unit 60, and an optical connecting unit 70. The characteristic changing part 50 is arranged in the characteristic light-guiding member 40 and configured to change the optical characteristic of the light guided by the light-guiding member 40, in accordance with how much the characteristic light-guiding member 40 is bent. The detecting unit 60 detects the light changed in optical characteristic by the characteristic changing part 50 and guided by the characteristic light-guiding member 40. The optical connecting unit 70 optically connects the light supplying/guiding member 30, the characteristic light-guiding member 40 and the detecting unit 60.

As shown in FIG. 1B, the light source 20 is optically connected to the light supplying/guiding member 30. The light emitted from the light source 20 is applied to the light supplying/guiding member 30. The light source 20 has, for example, a laser for emitting a laser beam or an LED light source for emitting an LED beam.

As shown in FIG. 1B, the light supplying/guiding member 30 has one end part 31a optically connected to the light source 20, and the other end part 31b optically connected to the optical connecting unit 70. The light supplying/guiding member 30 has, for example, flexibility. The light supplying/guiding member 30 has, for example, an optical fiber.

As shown also in FIG. 1B, the characteristic light-guiding member 40 has an end part 41a optically connected to the optical connecting unit 70, and the other end part 41b having a reflecting part 42. The reflecting part 42 reflects the light guided from the end part 41a, back to the end part 41a. The reflecting part 42 has, for example, a mirror.

The characteristic light-guiding member 40 has, for example, flexibility. The characteristic light-guiding member 40 has, for example, an optical fiber. As shown in FIG. 1C and FIG. 1D, the characteristic light-guiding member 40 has a core 43a, a cladding 43b covering the core 43a, and a jacket 43c for covering the cladding 43b and protecting the cladding 43b. The cladding 43b and the jacket 43c are cut in part, making a slit. In the slit, the characteristic changing part 50 is arranged. The characteristic changing part 50 is thus embedded in the characteristic light-guiding member 40. The inner circumferential surface of the characteristic changing part 50 contacts the core 43a. The outer circumferential surface of the characteristic changing part 50 does not protrude from the outer circumferential surface of the jacket 43c in a radial direction of the characteristic light-guiding member 40. Rather, it is flush with the outer circumferential surface of the jacket 43c. The sides of the characteristic changing part 50 contact the sides of the cladding 43b and the sides of the jacket 43c. The characteristic changing part 50 need not fill up the slit, and may have appropriate hardness and appropriate thickness. In this case, the characteristic changing part 50 has the thickness corresponding to the reaction of light of the characteristic changing part 50.

The characteristic changing part 50 may have, for example, a light absorbing part for absorbing light. In this case, the amount of light the characteristic changing part 50 absorbs depends on how much the characteristic light-guiding member 40 is bent. If the characteristic light-guiding member 40 is bent upwards, positioning the characteristic changing part 50 inside the characteristic light-guiding member 40 so bent, the characteristic changing part 50 will absorb less light than in the case where the characteristic light-guiding member 40 extends straight. If the characteristic light-guiding member 40 is bent downwards, positioning the characteristic changing part 50 outside the characteristic light-guiding member 40 so bent, the characteristic changing part 50 will absorb more light than in the case where the characteristic light-guiding member 40 extends straight. As the amount of light the characteristic changing part 50 absorbs increases or decreases, the amount of light propagates to the detecting unit 60 changes.

Thus, the characteristic changing part 50 changes the optical characteristic in accordance with, for example, how much the characteristic light-guiding member 40 is bent. As shown in FIG. 1B, the characteristic changing part 50 is arranged at a desirable point in the lengthwise direction of the characteristic light-guiding member 40, for example at the other end part 41b of the characteristic light-guiding member 40.

As shown in FIG. 1C, the characteristic light-guiding member 40 including the characteristic changing part 50 is covered with a protective member 43d and is protected by the protective member 43d. The protective member 43d may cover only the characteristic changing part 50, as shown in FIG. 1D. Thus, the protective member 43d only needs to cover and protect at least the characteristic changing part 50.

The characteristic light-guiding member 40 may be either integral with, or a member independent of, the light supplying/guiding member 30.

As shown in FIG. 1A and FIG. 1B, the optical connecting unit 70 has a light branching unit 71 and a substrate part 79. The light branching unit 71 branches the light emitted from the light source 20 to the characteristic light-guiding member 40, and branches the light guided by the characteristic light-guiding member 40 to the detecting unit 60. The substrate part 79 has a light guiding path 75 that includes the light branching unit 71.

As shown in FIG. 1B, the light branching unit 71 is branched into two end parts 73a, and other end part 73b. The end 731a of the end part 73a is optically connected to the other end part 31b of the light supplying/guiding member 30. The other end 73b is optically connected to one end part 41a of the characteristic light-guiding member 40. The other end 731b of the end part 73a is optically connected to the detecting unit 60. The light branching unit 71 can therefore guide the light by guided the light supplying/guiding member 30 to the characteristic light-guiding member 40, and guide the light by guided the characteristic light-guiding member 40 to the detecting unit 60. The light branching unit 71 prevents the light guided by the light supplying/guiding member 30 from propagating to the detecting unit 60, and prevents the light guided by the characteristic light-guiding member 40 from propagating back to the light supplying/guiding member 30. The light branching unit 71 therefore functions as light guiding path 75. The light branching unit 71 is composed of a film having a low refractive index and two films having a high refractive index and sandwiching the film having the low refractive index.

The light source 20 and the detecting unit 60 are arranged at the other end part 73a of the light branching unit 71. The characteristic light-guiding member 40 including the characteristic changing part 50 is arranged at the other end 73b of the light branching unit 71. The optical sensor 10 is arranged so that the light emitted from the light source 20 is reflected at the reflecting part 42 used as a relay point and then guided to the detecting unit 60.

The substrate part 79 has a recess part 79a. In the recess part 79a, the other end part 31b of the light supplying/guiding member 30 and the end part 41a of the characteristic light-guiding member 40 are held, whereby the light branching unit 71 is optically connected to the light supplying/guiding member 30, characteristic light-guiding member 40 and detecting unit 60. The recess part 79a is, for example, a V groove or a U groove. Since the other end part 31b of the light supplying/ guiding member 30 and the end part 41a of the characteristic light-guiding member 40 are held in the recess part 79a, the core (not shown) of the light supplying/guiding member 30 is optically connected to the core 73d of the light branching unit 71. As a result, the core 43a of the characteristic light-guiding member 40 is optically connected to the core 73d of the light branching unit 71. At this point, the other end part 31b of the light supplying/guiding member 30 and the end part 41a of the characteristic light-guiding member 40 are mounted on the substrate part 79. The other end part 31b of the light supplying/guiding member 30, the end part 41a of the characteristic light-guiding member 40, and the detecting unit 60 may be pushed by a member (not shown), secured to the substrate part 79 and optically connected to the light branching unit 71.

The substrate part 79 is made of at least one material selected from the group consisting of a semiconductor, glass, resin, ceramic, hard material (e.g., Si) and flexible material.

As shown in FIG. 1B, the detecting unit 60 is directly mounted on the substrate part 79. The characteristic changing part 50 may have a light absorbing part. If this is the case, the detecting unit 60 detects the change in the amount of light which occurs in the characteristic changing part 50, and eventually detects how much the characteristic light-guiding member 40 has been bent.

[Operation]

The light source 20 emits light. The light is applied to the light supplying/guiding member 30 and guided by the light supplying/guiding member 30 to the optical connecting unit 70. At this point, the light branching unit 71 branches the light to the characteristic light-guiding member 40. The light is applied to the characteristic light-guiding member 40, and guided by the characteristic light-guiding member 40. Thus, the light propagates from the end 73a of the light branching unit 71 to the other end 73b thereof.

At this point, the optical characteristic of the light is changed by the characteristic changing part 50. This change of the optical characteristic corresponds to the bending of the characteristic light-guiding member 40. That part of the light which has changed in optical characteristic, and the other part of the light which has not changed in optical characteristic, are guided by the characteristic light-guiding member 40 to the reflecting part 42 and reflected by the reflecting part 42. A part of the light so reflected is changed again in optical characteristic by the characteristic changing part 50. Thus, the characteristic changing part 50 changes optical characteristic of the light two times. That part of the light which has changed in optical characteristic, and the remaining part of the light which has not change in optical characteristic are guided by the characteristic light-guiding member 40 to the optical connecting unit 70. At this point, the light is branched by the light branching unit 71 to the detecting unit 60. That is, the light is applied to the detecting unit 60. Thus, the light returns from the other end 73b of the light branching unit 71 to the end 73a thereof.

The characteristic changing part 50 may have a light absorbing part. In this case, the amount of light changes twice, each time in accordance with the bending of the characteristic light-guiding member 40. The light thus changed in amount is detected by the detecting unit 60. Thus, the detecting unit 60 detects the amount of light changed in the characteristic changing part 50 and hence detects how much the characteristic light-guiding member 40 has been bent.

In this embodiment, the light applied from the light source 20 is reflected at the reflecting part 42 including the characteristic changing part 50 and used as a relay point, and then propagates to the detecting unit 60.

[Advantages]

In this embodiment, the light branching unit 71 thus branches light to the characteristic light-guiding member 40 and the detecting unit 60. That is, the light is reflected and then propagates in the opposite direction in this embodiment. The optical sensor 10 can therefore be made smaller than otherwise. The optical sensor 10 according to this embodiment can be incorporated in a small high-precision device (not shown).

The small high-precision device may be, for example, a thin and long member such as the insertion section of a medical endoscope, the insertion section of an industrial endoscope, a manipulator, or a catheter. In this case, this embodiment is particularly useful, because the light is reflected and then propagates in the opposition direction.

Figure 5A:
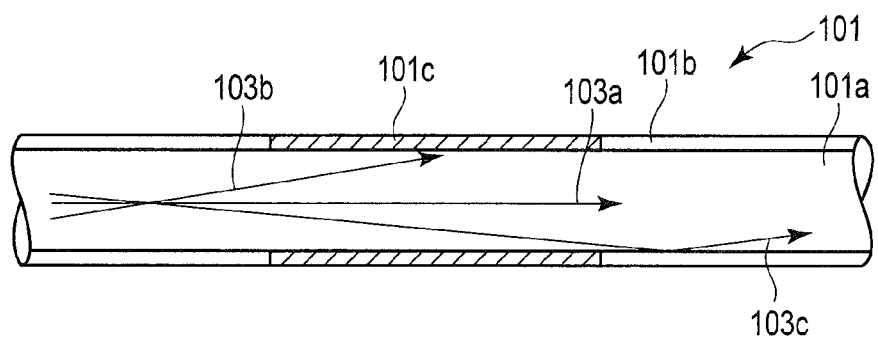
FIG. 5A is a diagram showing an optical fiber of the general type, which extends straight.
Figure 5B:
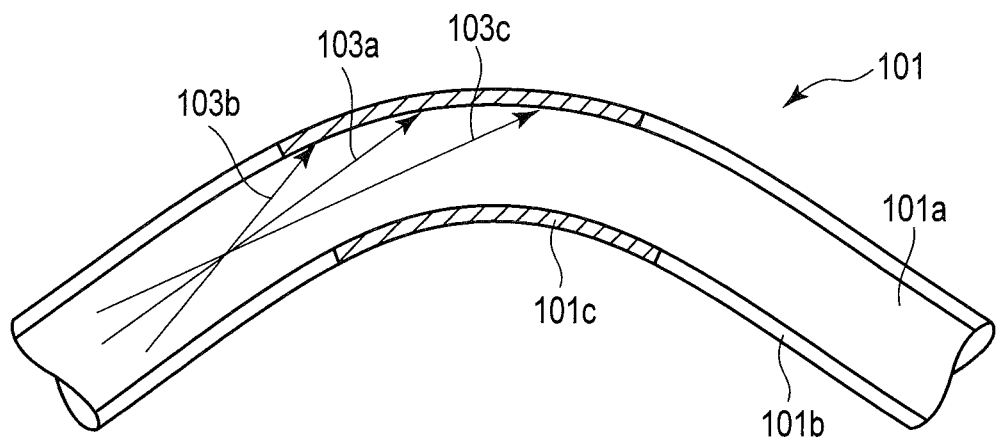
FIG. 5B is a diagram showing the optical fiber shown in FIG. 5A, which is bent.
Figure 5C:
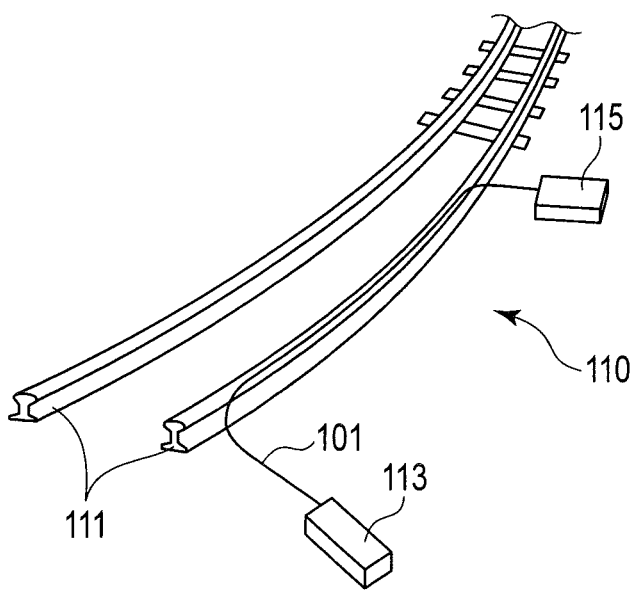
FIG. 5C is a diagram showing a curvature measuring device which is a representative optical sensor having the optical fiber shown in FIG. 5A.

As shown in, for example, FIG. 5C, a laser light source 113 may be connected to one end part of an optical fiber 101, and a photoelectric transducer device 115 is arranged at the other end part of the optical fiber 101. In this case, light propagates in one direction only. If the optical sensor 10 is used in combination with a small high-precision device, a part of the optical sensor 10 will be inevitably arranged outside the high-precision device. The optical sensor 10 has low installation freedom.

However in this embodiment, the light is reflected and then propagates back, and only the characteristic light-guiding member 40 including the characteristic changing part 50 needs to be arranged in a small high-precision device. The freedom of positioning of the optical sensor 10 can therefore be maintained.

Further, the optical sensor 10 according to this embodiment can be made small, because both the light source 20 and the detecting unit 60 are arranged at one end part 73a of the light branching unit 71.

The optical sensor 10 according to this embodiment can be made small and simple because the light branching unit 71 functions as light guiding path 75.

Further, since the optical connecting unit 70 is optically connected, on the substrate part 79, to the light supplying/ guiding member 30, characteristic light-guiding member 40 and detecting unit 60, the optical sensor 10 according to this embodiment can be manufactured with less labor than otherwise, and can be mass-produced at low cost.

Still further, the substrate part 79 increases the strength of the small optical sensor 10. Since the substrate part 79 is made of a flexible material, the light branching unit 71 can be bent. This increases the freedom of positioning of the optical sensor 10.

Moreover, the characteristic changing part 50, which is arranged on the characteristic light-guiding member 40 only, changes the optical characteristic in accordance with the bending of the characteristic light-guiding member 40. Therefore, the optical characteristic can be reliably changed in accordance with the bending of the characteristic light-guiding member 40. In addition, the detecting unit 60 can reliably detect how much the characteristic light-guiding member 40 is bent. Further, the detecting unit 60 can detect the bending of the characteristic light-guiding member 40, irrespective of the bending or twisting of the light supplying/guiding member 30.

In this embodiment, the light source 20 may be mounted on the substrate part 79 and may thereby be optically connected directly to the optical connecting unit 70, as shown in FIG. 1E.

In this embodiment, the reflecting part 42 can reliably reflect the light. This enhances the detection precision of the detecting unit 60, and prevents the light from radiating outside from the other end part 41b of the characteristic light-guiding member 40. The light may be reflected by the other end part 41b of the characteristic light-guiding member 40. In this case, the reflecting part 42 can be dispensed with, possibly reducing the manufacturing cost of the optical sensor 10.

The detecting unit 60 is mounted on the substrate part 79 in the present embodiment. Nonetheless, the detecting unit 60 need not be mounted on the substrate part 79, and may be optically connected, like the light source 20, to other end 731b of the end part 73a of the light branching unit 71 by a depending light guiding member (e.g., optical fiber, not shown).

Moreover, the characteristic changing part 50 may be a wavelength-changing member (e.g., phosphor) that changes the wavelength of the light. If this is the case, the amount of the light changed in wavelength by the characteristic changing part 50 differs in accordance with how much the characteristic light-guiding member 40 is bent. If the characteristic light-guiding member 40 is bent upwards, positioning the characteristic changing part 50 inside the characteristic light-guiding member 40, the amount of light changed in wavelength by the characteristic changing part 50 will decrease more than in the case the characteristic light-guiding member 40 extends straight. If the characteristic light-guiding member 40 is bent downwards, positioning the characteristic changing part 50 outside the characteristic light-guiding member 40, the amount of light changed in wavelength by the characteristic changing part 50 will increase more than in the case the characteristic light-guiding member 40 extends straight. Thus, the amount of light propagating to the detecting unit 60 changes by the amount of light that the characteristic changing part 50 changes the wavelength is changed.

In this embodiment, the characteristic changing part 50 changes the optical characteristic in accordance with, for example, the bending of the characteristic light-guiding member 40. Instead, the characteristic changing part 50 may change the optical characteristic in accordance with, for example, at least one physical amount selected from the group consisting of the bending direction of the characteristic light-guiding member 40, the bending amount of a high-precision device, the bending direction of the high-precision device and the operating amount of the high-precision device.

Second Embodiment

[Configuration]

The second embodiment will be described as to only the configuration features distinguishing this embodiment from the first embodiment, with reference to FIG. 2A and FIG. 2B.

As shown in FIG. 2B, the light supplying/guiding member 30 is monolithically formed on the substrate part 79. The configuration need not be limited to this, nevertheless. At least of the light source 20, the light supplying/guiding member 30 and detecting unit 60a, 60b and 60c may be monolithically formed on the substrate part 79. If the light source 20 is monolithically mounted on the substrate part 79, it may be directly connected to the optical connecting unit 70. If the light supplying/guiding member 30 is connected to the optical connecting unit 70, the light source 20 and the light supplying/guiding member 30 may be monolithically mounted on the substrate part 79.

As FIG. 2A and FIG. 2B show, characteristic changing parts 50a, 50b and 50c are arranged. The characteristic changing parts 50a, 50b and 50c have a light absorbing part each. The absorbing parts of the characteristic changing parts 50a, 50b and 50c absorb lights of different wavelengths each other. That is, wavelength of light A that he characteristic changing parts 50a is absorbed, wavelength of light B that he characteristic changing parts 50b is absorbed and wavelength of light C that he characteristic changing parts 50c is absorbed are differed each another. This is because the characteristic changing parts 50a, 50b and 50c change the optical characteristics of the light A, light B and light C, respectively, to different values.

In this embodiment, the light source 20 emits light A, light B and light C independently of one another. Since only one light supplying/guiding member 30 is provided, the light A, B and C are guided as a synthesized light by the light supplying/guiding member 30. The light source 20 emits light containing the lights A, B and C. The light supplying/guiding member 30 and the characteristic light-guiding member 40 may be formed of optical fibers that can guide light in a broad band.

As shown in FIG. 2B, the characteristic changing parts 50a and 50b are arranged on, for example, an upper part of the characteristic light-guiding member 40, in the diameter direction of the characteristic light-guiding member 40. The characteristic changing part 50b is arranged closer to the reflecting part 42 than the characteristic changing part 50a. Thus, a position of the characteristic changing part 50a and a position of the characteristic changing part 50b are different from each other in the axis of the characteristic light-guiding member 40.

As shown in FIG. 2B, the characteristic changing part 50c is arranged on the right in the diameter direction of the characteristic light-guiding member 40. The characteristic changing part 50c is spaced from the characteristic changing part 50a by, for example, 90° in the circumferential direction of the characteristic light-guiding member 40.

Since the characteristic changing parts 50a, 50b and 50c are so arranged, detecting units 60 detect not only bending amount of characteristic light-guiding member 40, but also bending position of the member 40.

Since the characteristic changing parts 50a and 50b are so arranged as specified above, the detecting units 60 can detect that bending amount of the characteristic light-guiding member 40 at different positions in the axial direction of the characteristic light-guiding member 40.

Since the characteristic changing parts 50*a* and 50*b* are so arranged as specified above, the detecting units 60 can detect the direction in which the characteristic light-guiding member 40 is bent.

As shown in FIG. 2A and FIG. 2B, detecting units 60*a*, 60*b* and 60*c* are arranged at the detecting unit 60 in the present embodiment.

For example, the detecting unit 60*a* has a band selecting unit 61*a* associated with the characteristic changing part 50*a* and configured to select only the light whose optical characteristic has been changed by the characteristic changing part 50*a*. The characteristic changing part 50*a* detects the light selected by the band selecting unit 61*a*, therefore detects bending amount and bending position of the characteristic light-guiding member 40.

The detecting unit 60*b* has a band selecting unit 61*b* associated with the characteristic changing part 50*b* and configured to select only the light whose optical characteristic has been changed by the characteristic changing part 50*b*. The characteristic changing part 50*b* detects the light selected by the band selecting unit 61*b*, therefore detects bending amount and bending position of the characteristic light-guiding member 40.

The detecting unit 60*c* has a band selecting unit 61*c* associated with the characteristic changing part 50*c* and configured to select only the light whose optical characteristic has been changed by the characteristic changing part 50*c*. The characteristic changing part 50*c* detects the light selected by the band selecting unit 61*c*, therefore detects bending amount and bending position of the characteristic light-guiding member 40.

Thus, the detecting units 60 are used in the same number as the characteristic changing parts 50. More precisely, the detecting units 60*a* 60*b* and 60*c* have band selecting units 61*a*, 61*b* and 61*c*, respectively, which select the lights whose optical characteristics have been changed by the characteristic changing parts 50*a*, 50*b* and 50*c*, respectively. The detecting units 60*a*, 60*b* and 60*c* detect the lights selected by the band selecting units 61*a*, 61*b* and 61*c*, respectively.

The band selecting units 61*a*, 61*b* and 61*c* are mounted on the substrate part 79. Alternatively, they may be monolithically formed with the substrate part 79. Each of the band selecting units 61*a*, 61*b* and 61*c* is at least one of a dispersion-type spectrometer and an interference-type spectrometer. The dispersion-type spectrometer has at least one of a prism, a grating and both. The interference-type spectrometer has, a for example a color filter that allows the passage of light falling in a desirable wavelength range. The interference-type spectrometer only needs to limit the band.

This embodiment has light branching units 71*a* and 71*b*.

The light branching unit 71*a* branches the light guided by the light supplying/guiding member 30, to the characteristic light-guiding member 40, and branches the light guided by the characteristic light-guiding member 40, to the light branching unit 71*b*.

The light branching unit 71*b* branches this light branched by the light branching unit 71*a* to the band selecting units 61*a*, 61*b* and 61*c*.

The light branching units 71*a* and 71*b* have, for example, an optical fiber functioning as light guiding path 75.

[Operation]

The light source 20 emits, for example, two lights A, B and C independently of each other. These lights A, B and C are is applied to the light supplying/guiding member 30 in synthesized state. The light supplying/guiding member 30 guides the light to the optical connecting unit 70. The lights A, B and C are branched by the light branching unit 71*a* to the characteristic light-guiding member 40. The lights A, B and C are applied to the characteristic light-guiding member 40. The characteristic light-guiding member 40 guides the lights A, B and C to the reflecting part 42. The reflecting part 42 reflects the lights A, B and C.

At this point, the characteristic changing parts 50*a* change the optical characteristic (e.g., amount) of the light A two times, as in the first embodiment. The light branching unit 71*a* branches the light A, so changed in optical characteristic, to the light branching unit 71*b*. The light branching unit 71*b* branches the light A to the band selecting units 61*a*, 61*b* and 61*c*. The light A is selected by the band selecting unit 61*a* and then detected by the detecting unit 60*a*. The light A is branched to the band selecting units 61*b* and 61*c*, too, but is not selected by the band selecting units 61*b* and 61*c* nor detected by the detecting units 60*b* and 60*c*, respectively.

The characteristic changing part 50*b* changes the optical characteristic of the light B twice. The light B is selected by the band selecting unit 61*b* and detected by the detecting unit 60*b*.

The characteristic changing part 50*c* changes the optical characteristic of the light C two times. The light C is selected by the band selecting unit 61*c* and detected by the detecting unit 60*c*.

[Advantages]

In this embodiment, the characteristic changing parts 50*a*, 50*b* and 50*c* are used, making it possible to detect how much and where the characteristic light-guiding member 40 is bent. Thus, one characteristic light-guiding member 40 suffices to achieve detection at some points that the number of characteristic light-guiding member 40 is not increased. Further, the characteristic changing parts 50*a* and 50*b* can detect how much the characteristic light-guiding member 40 is bent at different positions in the axial direction of the characteristic light-guiding member 40. Still further, the characteristic changing parts 50*a* and 50*c* can detect in which direction the characteristic light-guiding member 40 is bent. Thus, various information items can be acquired in this embodiment.

In this embodiment, the characteristic changing parts 50*a*, 50*b* and 50*c* and the band selecting units 61*a*, 61*b* and 61*c* cooperate to detect the bending amount of the characteristic light-guiding member 40. Also, they cooperate in detecting the position where the characteristic light-guiding member 40 is bent.

In this embodiment, in the light source 20, the light supplying/guiding member 30 and the detecting units 60*a*, 60*b* and 60*c*, or at least one of these components is monolithically mounted on the substrate part 79. Further, the band selecting units 61*a*, 61*b* and 61*c* are monolithically mounted on the substrate part 79. Therefore, the optical sensor 10 according to this embodiment can be made small, and the connection of its components can be simple, and the optical sensor 10 can be made at low cost.

In this embodiment, the band selecting units 61*a*, 61*b* and 61*c* can detect the lights A, B and C, independently and respectively. This helps to make the optical sensor 10 small and to manufacture the same at low cost.

The characteristic changing parts 50*a*, 50*b* and 50*c* may be constituted by wavelength changing members.

In this case, the light source 20 emits the lights A, B and C, independently of one another, or emits light including the lights A, B and C.

In this embodiment, light sources 20*a*, 20*b* and 20*c* may be provided, which emits lights A, B and C, respectively, as shown in FIG. 2C. Further, light supplying/guiding member 30*a*, 30, and 30*c* may be provided, which are optically connected to the light sources 20*a*, 20*b* and 20*c*, respectively, and guide lights A, B and C, respectively. The light applying/guiding members 30a, 30, and 30c are fitted in the recess part 79a and are optically connected to the light branching unit 71a. The nodes of the light applying/guiding members 30a, 30, and 30c and the light branching unit 71a are covered with a cover 90.

In this embodiment, the light applying/guiding members 30a, 30, and 30c can be easily axially aligned, because they are fitted in the recess part 79a. Moreover, the cover 90 can protect the nodes of the light applying/guiding members 30a, 30, and 30c.

Third Embodiment

[Configuration]

Figure 3:
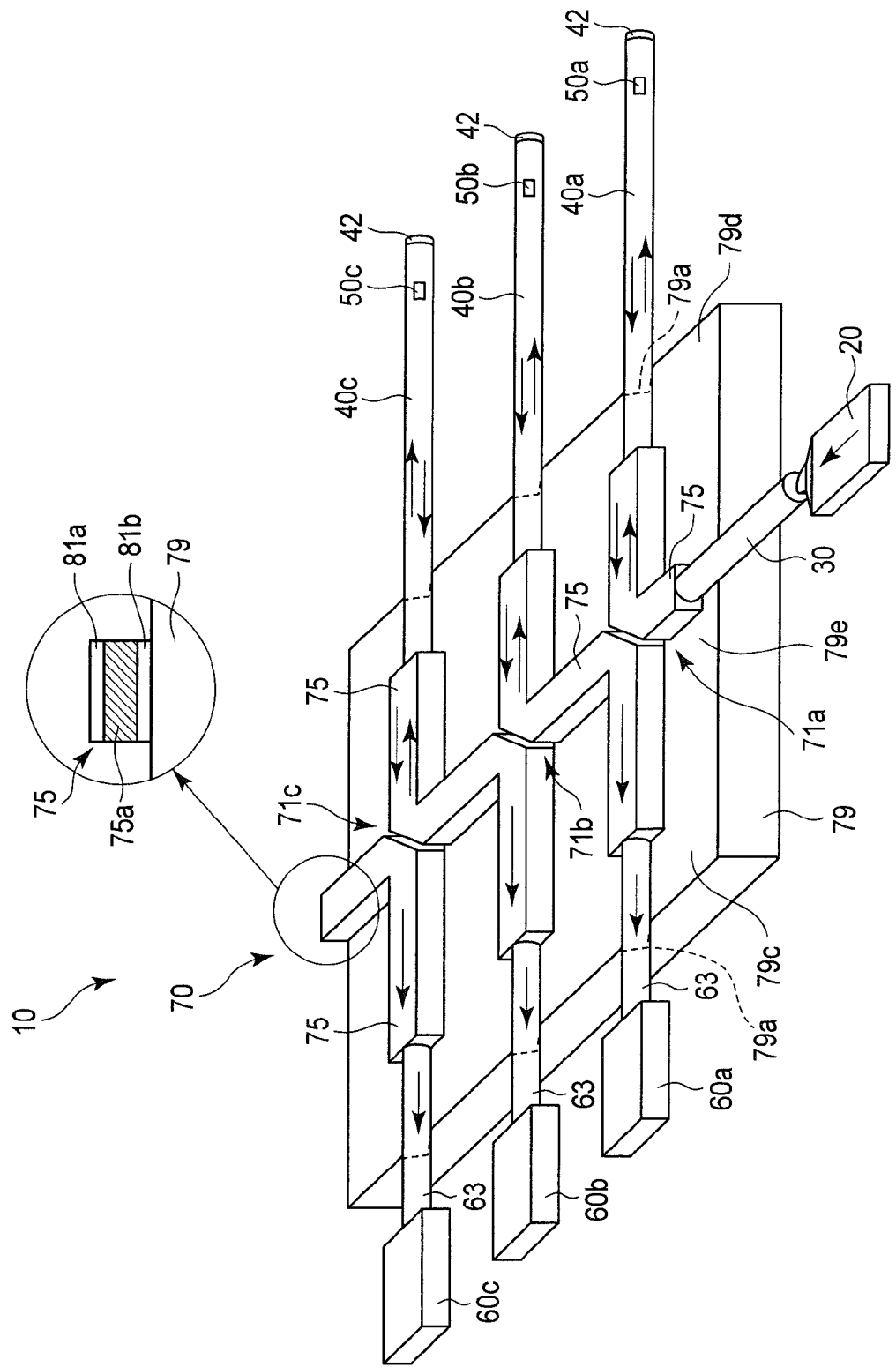
FIG. 3 is a schematic diagram showing an optical sensor according to a third embodiment of this invention.

The third embodiment will be described with reference to FIG. 3 as to only the configuration features distinguishing the embodiment from the first and second embodiments. That is, it will be described how the light source 20, light supplying/guiding member 30, characteristic light-guiding members 40a, 40b and 40c and detecting units 60a, 60b and 60c are arranged in a specific relation.

One light source 20 and one light supplying/guiding member 30 are provided. The light source 20 and the light supplying/guiding member 30 are arranged at one side 79e of the substrate part 79, not one end part 79c or the other end part 79d. The light supplying/guiding member 30 extends, for example, at right angles to the line connecting the end part 79c and the other end part 79c.

The characteristic light-guiding members 40a, 40b and 40c are arranged at the other end part 79d of the substrate part 79. The characteristic light-guiding members 40a, 40b and 40c are optically connected to the light guiding path 75 of the optical connecting unit 70. When the characteristic light-guiding members 40a, 40b and 40c are fitted in the recess part 79a, the cores (not shown) of the characteristic light-guiding members 40a, 40b and 40c is optically connected to the core 75a of the light guiding path 75. The characteristic light-guiding members 40a, 40b and 40c are arranged, for example, along a line connecting the end part 79c and other end part 79d of the substrate part 79. The characteristic light-guiding members 40a, 40b and 40c are arranged parallel to one another.

The detecting units 60a, 60b and 60c are arranged at the other end part 79d side of the substrate part 79. The detecting units 60a, 60b and 60c are optically connected to the light guiding path 75 of the optical connecting unit 70, by a detecting light applying/guiding member 63 that is an optical fiber. When the detecting light applying/guiding member 63 are fitted in the recess part 79a, the cores (not shown) of the detecting light applying/guiding member 63 is optically connected to the core 75a of the light guiding path 75. The detecting light applying/guiding member 63 is arranged, extending along, for example, a line connecting the end part 79c and other end part 79d of the substrate part 79.

Thus, the light source 20, light supplying/guiding member 30, characteristic light-guiding members 40a, 40b and 40c and detecting units 60a, 60b and 60c and detecting light applying/guiding member 63 are arranged in a T-shaped pattern.

It will be explained how the characteristic light-guiding members 40a, 40b and 40c, the detecting units 60a, 60b and 60c and the optical connecting unit 70 are configured.

The characteristic light-guiding member 40a has a characteristic changing part 50a, the characteristic light-guiding member 40b has a characteristic changing part 50b, and the characteristic light-guiding member 40c has a characteristic changing part 50c. The characteristic light-guiding members (40a to 40c), characteristic changing parts (50a to 50c) and light branching units (71a to 71c) are provided in the same number, for example 3. In this case, the light source 20 emits light including the lights A, B and C.

The optical connecting unit 70 further has the light guiding path 75, which is, for example, an optical fiber. The light guiding path 75 is optically connected to the characteristic light-guiding members 40a, 40b and 40c and the detecting light applying/guiding member 63. Thus, the light guiding path 75 is arranged along a straight line connecting the end part 79c and the other end part 79d, and also along a straight line at right angles to that straight line. The light guiding path 75 guided to the characteristic light-guiding members 40a, 40b and 40c light guided by the light supplying/guiding member 30 and guided to the detecting light applying/guiding member 63 light guided by the characteristic light-guiding members 40a, 40b and 40c.

The light branching units 71a, 71b and 71c are each a combination of a reflecting/transmitting part for reflecting and transmitting light or reflecting part for reflecting light, and a transmitting part for transmitting light. The light branching units 71a, 71b and 71c are arranged on the light guiding path 75. The light branching units 71a, 71b and 71c extend along a straight line at right angles to the straight line connecting the end part 79c and the other end part 79d. The light branching units 71a, 71b and 71c have a groove each. The groove inclines at a desirable angle to the straight line extending from the end part 79c to the other end part 79d.

As described above, the light branching units 71a, 71b and 71c are provided in the same number as the characteristic light-guiding members 40a, 40b and 40c. The light branching units 71a, 71b and 71c need to branch the light emitted from the light source 20 and guided by the light supplying/guiding member 30 to the three characteristic light-guiding members 40a, 40b and 40c. This is why the light branching units 71a, 71b and 71c control the light-branching ratio so that the light may propagate to the characteristic light-guiding members 40a, 40b and 40c. The control is performed in accordance with at least one selected from the group consisting of the configuration of the reflecting/transmitting parts (not shown) of the light branching units 71a, 71b and 71c, the angle of the above-mentioned grooves (not shown) and the refractive index of the material filling the grooves. Each of the light branching units 71a, 71b and 71c is configured to reflect the light and transmit the light. As described above, the light source 20, light supplying/guiding member 30, characteristic light-guiding members 40a, 40b and 40c and detecting units 60a, 60b and 60c and detecting light applying/guiding member 63 are arranged in a T-shaped pattern. Therefore, when the light branching units 71a, 71b and 71c reflect the light, the light branching units 71a, 71b and 71c branched the light so that the light branching units 71a, 71b and 71c reflect the light at 90° to the direction in which the light is applied to them, thus making the light propagate to the characteristic light-guiding members 40a, 40b and 40c. When the light branching units 71a, 71b and 71c is transmitted the light, the light branching units 71a, 71b and 71c branches the light, so that the light is applied to the branching units 71a, 71b and 71c not inclined thereto, and passes through the light branching units 71a, 71b and 71c.

The light guiding path 75 includes the light branching units 71a, 71b and 71c is sandwitched a substrate part 81a and 81b. The substrate parts 81a and 81b are made of, for example, at least one material selected from the group consisting of Si, SiOx, Parlylen, silicon resin and polyimide. The refractive index of the substrate part 81a is higher than that of the substrate part 81b.

The substrate part 79 is made of at least one of a semiconductor, glass, resin, ceramic, hard material, for example Si and flexible material.

The light source 20, characteristic light-guiding member 40, detecting unit 60 and light branching unit 71 may be used in various numbers. The light source 20 may be used in number L, the characteristic light-guiding member 40 may be used in number M, and the detecting unit 60 may be used in number N. That is, L≥1, M≥1 and N≥1. In this case, at least one of L≠M and L≠N is hold. Further, M and N may be the same number or different numbers. The light branching unit 71 is used in a desirable number that accords with the number of characteristic light-guiding members 40 used and the number of detecting units 60 used.

[Operation]

The light source 20 emits light containing, for example, lights A, B and C. These lights are applied to the light supplying/guiding member 30. The light supplying/guiding member 30 guides the lights to the light guiding path 75.

The light is guided from the light guiding path 75 to the branching units 71a. The branching unit 71a reflects the light by 90°, branching the light to the characteristic light-guiding members 40a. The light branched is guided by the light guiding path 75 to the characteristic light-guiding members 40a. The light is then reflected by the reflecting part 42. At this point, the light A contained in the light is changed twice in optical characteristic (e.g., amount) by the characteristic changing part 50a, as in the first embodiment. The light containing the light A, now changed in optical characteristic, is applied from the characteristic light-guiding members 40a through the light guiding path 75 to the branching unit 71a, passes through the branching unit 71a, and is applied to the detecting light applying/guiding member 63 through the light guiding path 75. The detecting light applying/guiding member 63 guides the light containing the light A. The light is detected by the detecting unit 60a.

The light passes through the branching unit 71a, is reflected by the branching unit 71b by 90°, is thereby branched to the characteristic light-guiding member 40b through the light guiding path 75 and is guided by the characteristic light-guiding member 40b. The light is then reflected by the reflecting part 42. At this point, the light B contained in the light is changed twice in optical characteristic (e.g., amount) by the characteristic changing part 50b, as in the first embodiment. The light containing the light B so changed in optical characteristic is applied through the light guiding path 75 to the branching unit 71b, passes through the branching unit 71b, and is applied through the light guiding path 75 to the detecting light applying/guiding member 63. The detecting light applying/guiding member 63 guides the light containing the light B. The light is detected by the detecting unit 60b.

The light passes though the branching units 71a and 71b, is reflected by 90° by the light branching unit 71c and thereby branched the characteristic light-guiding member 40c through the light guiding path 75, and is guided by the characteristic light-guiding member 40c. Then, the light is reflected by the reflecting part 42. At this point, the light is changed twice in optical characteristic (e.g., amount) by the characteristic changing part 50c, as in the first embodiment. The light containing the light C so changed in optical characteristic is applied from the characteristic light-guiding member 40c through the light guiding path 75 to the branching unit 71c, passes through the branching unit 71c, and is applied through the light guiding path 75 to the detecting light applying/guiding member 63. The detecting light applying/guiding member 63 guides the light containing the light C. The light is detected by the detecting unit 60c.

[Advantages]

In this embodiment, the characteristic light-guiding members 40a, 40b and 40c have characteristic changing parts 50a, 50b and 50c, respectively. The characteristic light-guiding members 40a, 40b and 40c can therefore provide some detecting points, which can enhance the detection accuracy. For example, the characteristic changing parts 50a, 50b and 50c are arranged at different positions in the axial directions of the characteristic light-guiding members 40a, 40b and 40c. This makes it possible to detect how much the characteristic light-guiding members 40a, 40b and 40c are bent at various positions.

In this embodiment, the branching units 71a, 71b and 71c can increase the freedom in light-branching configuration. Further, the branching units 71a, 71b and 71c can branch the light at high efficiency, which enhances the detection accuracy of the detecting units 60a, 60b and 60c.

In this embodiment, the branching units 71a, 71b and 71c can reflect light and allow the passage of light. The light containing lights A, B and C can therefore be reliably emitted. As a result, the light is branched to the characteristic light-guiding members 40a, 40b and 40c, it suffices to use only one light source 20, and the optical sensor 10 can therefore be made small and can be manufactured at low cost. Moreover, the branching ratio between the branching units 71a, 71b and 71c is used, predicting the ratio of light quantities the detecting units 60a, 60b and 60c will detect. This helps to control the optical sensor 10 easily.

Further, in this embodiment, the number of light sources 20 used can be smaller than the number of characteristic light-guiding members 40a, 40b and 40c, because the branching units 71a, 71b and 71c are used.

In this embodiment, the light source 20, light supplying/guiding member 30, characteristic light-guiding members 40a, 40b and 40c and detecting units 60a, 60b and 60c and detecting light applying/guiding member 63 can be arranged in a T-shaped pattern because the branching units 71a, 71b and 71c are used. This increase the freedom of positioning the optical sensor 10.

In this embodiment, the characteristic changing parts 50a, 50b and 50c need not be provided in the same number as the characteristic light-guiding members 40a, 40b and 40c. Rather, the characteristic light-guiding member 40a may have a plurality of characteristic changing parts 50. If this is the case, the detecting unit 60a, for example, have a plurality of band selecting units 61 corresponds to the characteristic changing parts 50. Alternatively, the detecting unit 60a may be arranged corresponds to the band selecting units 61, in one-to-one relation. This holds true of the characteristic light-guiding members 40b and 40c and the detecting units 60b and 60c. Thus, more information items can be detected than otherwise.

Fourth Embodiment

[Configuration]

The fourth embodiment will be described with reference to FIGS. 4A, 4B and 4C.

Figure 4B:
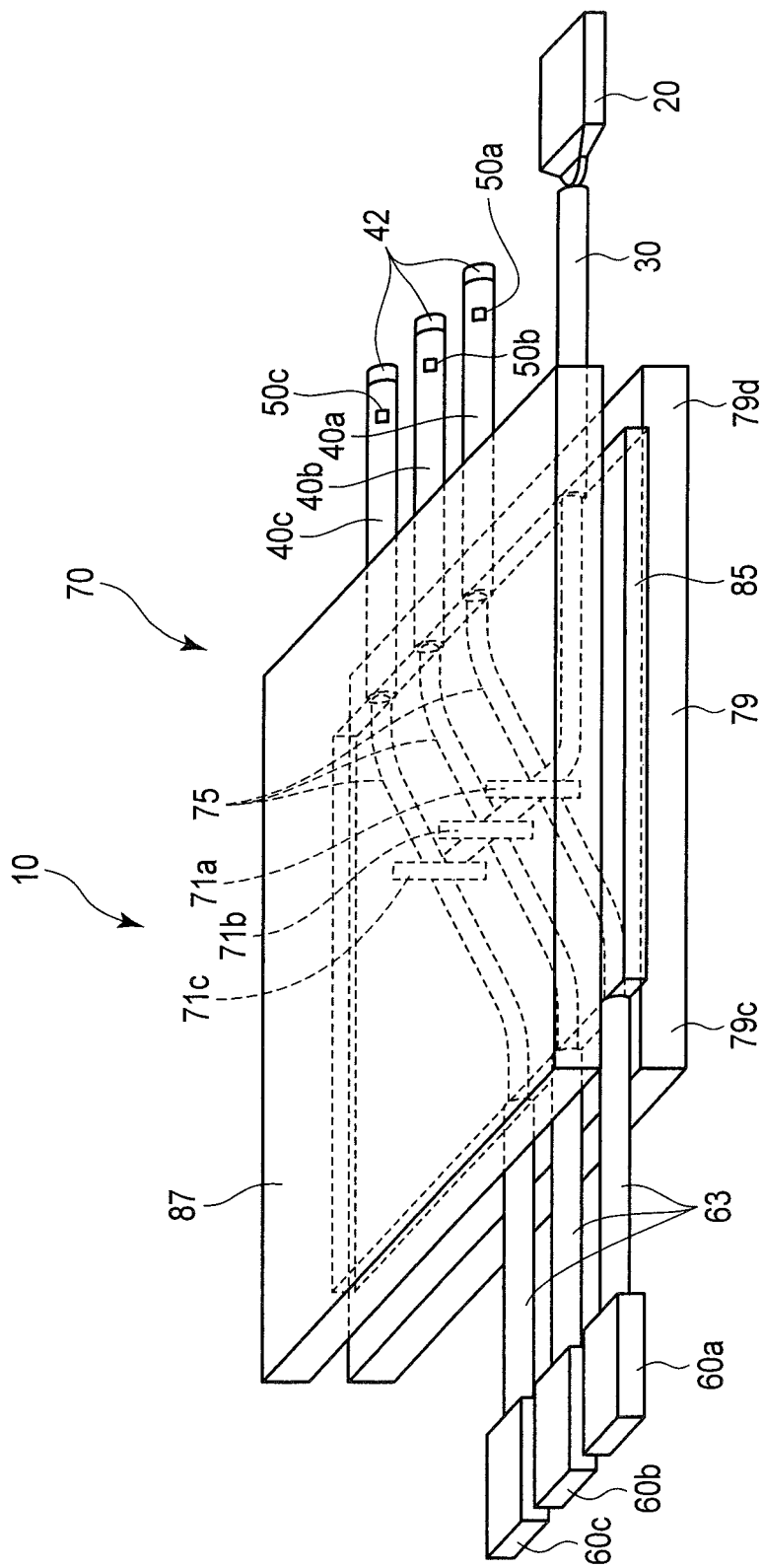
FIG. 4B is a schematic perspective view of the optical sensor shown in FIG. 4A.

As FIGS. 4A, 4B and 4C show, a light source 20 and a light supplying/guiding member 30 are arranged at the other end part 79d side of a substrate part 79.

As shown in FIG. 4C, an optical connecting unit 70 has, the substrate part 79 that is rectangular plate, a low-flexibility sheet 83a, a substrate part 85, a low-flexibility sheet 83b, and a hard-material plate 87. The low-flexibility sheet 83a is mounted on the substrate part 79. The substrate part 85 is mounted on the low-flexibility sheet 83a. On the substrate part 85, branching units 71a, 71b and 71c and light guiding paths 75 are arranged. The low-flexibility sheet 83b is mounted on the substrate part 85. The hard-material plate 87 is mounted on the low-flexibility sheet 83a.

The optical connecting unit 79 has recesses part 79a. The recesses part 79a hold the light supplying/guiding member 30, characteristic light-guiding members 40a, 40b and 40c and light applying/guiding members 63, securing them to the substrate part 79 and optically connecting them to the light guiding paths 75. When the light supplying/guiding member 30, characteristic light-guiding members 40a, 40b and 40c and light applying/guiding members 63 are fitted in the recesses part 79a, the light supplying/guiding member 30, characteristic light-guiding members 40a, 40b and 40c and light applying/guiding members 63 are fitted are optically connected to the light guiding paths 75. More specifically, the cores of the light supplying/guiding member 30, characteristic light-guiding members 40a, 40b and 40 and light applying/guiding members 63 are optically connected to the light guiding paths 75. The recesses part 79a is, for example, V grooves or U grooves.

The light applying/guiding members 63 are secured to one end part 79c of the substrate part 79. The light supplying/guiding member 30 and the characteristic light-guiding members 40a, 40b and 40c are secured to the other end part 79d side of the substrate part 79. The light supplying/guiding member 30 and the characteristic light-guiding members 40a, 40b and 40c are arranged, for example, parallel to one another. The characteristic light-guiding members 40a, 40b and 40c are arranged parallel to one another. The light supplying/guiding member 30, the characteristic light-guiding members 40a, 40b and 40c and the light applying/guiding members 63 are arranged in the same direction.

The branching units 71a, 71b and 71c are arranged in the light guiding paths 75, respectively. The branching units 71a, 71b and 71c are provided in the same number as the characteristic light-guiding members 40a, 40b and 40c. Each of the branching units 71a, 71b and 71c is composed of a transmitting part and a reflecting part. The branching units 71a, 71b and 71c reflect (branch) the lights guided by the light guiding paths 75 to the characteristic light-guiding members 40a, 40b and 40c. The characteristic light-guiding members 40a, 40b and 40c transmit (branch) the lights to the light guide member. The branching units 71a, 71b and 71c control the reflection-to-transmission ratio in accordance with their transmitting characteristic and reflecting characteristic and with the angles defined by the lights applied from the light supplying/guiding member 30 to the branching units 71a, 71b and 71c and the lights applied from the characteristic light-guiding members 40a, 40b and 40c to the branching units 71a, 71b and 71c. The branching units 71a, 71b and 71c are arranged such that each is inclined to the straight line connecting the ends part 79a and part 79d of the substrate part 79.

The angle defined by the light guiding paths 75 connecting the supplying/guiding member 30 to the branching units 71a, 71b and 71c and the light guiding paths 75 holding the branching units 71a, 71b and 71c and connecting the characteristic light-guiding members 40a, 40b and 40c to the light applying/guiding members 63 is smaller than 90° because of the branching units 71a, 71b and 71c. When the branching units 71a, 71b and 71c reflect the light, the branching units 71a, 71b and 71c reflect by an angle smaller than 90°, with respect to the direction in which they receive the light, because of light-reflecting characteristic of the branching units 71a, 71b and 71c.

The low-flexibility sheet 83a and 83b have a smaller refractive index than the branching units 71a, 71b and 71c. The low-flexibility sheets 83a and 83b sandwich the branching units 71a, 71b and 71c, preventing light from leaking from the branching units 71a, 71b and 71c.

The hard-material plate 87 protects the branching units 71a, 71b and 71c, the optical/mechanical connection of the branching units 71a, 71b and 71c and light supplying/guiding member 30, the optical/mechanical connection of the characteristic light-guiding members 40a, 40b and 40c and branching units 71a, 71b and 71c, and the optical/mechanical connection of the light-guiding members and branching units 71a, 71b and 71c. Further, the hard-material plate 87 strengthens the connection of the light supplying/guiding member 30, characteristic light-guiding members 40a, 40b and 40c, light applying/guiding members 63 and branching units 71a, 71b and 71c. The hard-material plate 87 is, for example, a transparent member of glass or the like.

[Operation]

This embodiment operates almost in the same way as the third embodiment. Therefore, how it operates will not be explained.

[Advantages]

In this embodiment, owing to the branching units 71a, 71b and 71c and the light guiding paths 75, the light source 20, light supplying/guiding member 30 and characteristic light-guiding members 40a, 40b and 40c can be arranged at the other end part 79d of the substrate part 79, and the light applying/guiding members 63 and detecting units 60a, 60b and 60c can be arranged at the end part 79c of the substrate part 79. In this embodiment, the branching units 71a, 71b and 71c can be arranged along lines inclined to the straight line connecting the end parts 79a and 79b of the substrate part 79 because of their transmitting characteristic and reflecting characteristic and their inclining angle. The distance between the end parts 79a and 79b can therefore be shorter than in the third embodiment, and the optical sensor 10 can be made smaller.

In this embodiment, the hard-material plate 87 can protect the optical and mechanical connection in the optical connecting unit 70, increasing the connection strength.

The light source 20 and the light supplying/guiding member 30 may be arranged at the end part 79c side of the substrate part 79. The light source 20 and detecting units 60a, 60b and 60c may be connected directly to the optical connecting unit 70.

The present invention is not limited to the embodiments described above. The components of any embodiment can be modified in various manners in reducing the invention to practice. Further, the components of any embodiment described above may be combined, if necessary, in various ways to make different inventions.

What is claimed is:

1. An optical sensor comprising:
   a light source configured to emit light;
   a characteristic light-guiding member configured to guide the light emitted from the light source;
   a characteristic changing part arranged in the characteristic light-guiding member and configured to change an optical characteristic of the light in accordance with how much the characteristic light-guiding member is bent;

a detecting unit configured to detect the light changed in optical characteristic by the characteristic changing part and guided by the characteristic light-guiding member; and an optical connecting unit configured to connect optically the light source, the characteristic light-guiding member and the detecting unit, wherein the optical connecting unit has a light branching unit configured to branch the light emitted from the light source to the characteristic light-guiding member, and to branch the light guided by the characteristic light-guiding member to the detecting unit.

2. The optical sensor according to claim 1, wherein a plurality of the characteristic changing parts are provided, each being configured to change the optical characteristic of the light by to a different value; the detecting unit is provided in the same number as the characteristic changing parts, each having a band selecting unit associated with one characteristic changing part and configured to select only the light whose optical characteristic has been changed by the associated characteristic changing part; and the detecting unit configured to detect the light selected by the band selecting unit in the detecting unit.

3. The optical sensor according to claim 2, wherein the light source is provided in number L, the characteristic changing part is provided in number M and the detecting units are provided in number N, where $L \geq 1$, $M \geq 1$ and $N \geq 1$, and at least one of $L \neq M$ and $L \neq N$ is hold.

4. The optical sensor according to claim 3, wherein each of the light sources further has a substrate part including the light branching unit, and at least one of the light source and detecting unit are monolithically mounted on the substrate part.

5. The optical sensor according to claim 4, wherein the band selecting unit is monolithically mounted on the substrate part.

6. The optical sensor according to claim 5, wherein the band selecting unit is composed of at least one of a dispersion-type spectrometer and an interference-type spectrometer.

7. The optical sensor according to claim 6, wherein the light branching unit reflects and transmits the light.

8. The optical sensor according to claim 7 wherein the substrate part of the substrate part is made of a flexible material.

* * * * *